United States Patent
Jackson

(10) Patent No.: US 10,426,657 B2
(45) Date of Patent: Oct. 1, 2019

(54) THERMAL DEVICE FOR TREATING BREASTFEEDING CONDITIONS

(71) Applicant: Rachel E. Jackson, Buffalo, NY (US)

(72) Inventor: Rachel E. Jackson, Buffalo, NY (US)

(73) Assignee: Rachel's Remedies, LLC, Buffalo, NY (US)

( * ) Notice: Subject to any disclaimer, the term of this patent is extended or adjusted under 35 U.S.C. 154(b) by 414 days.

(21) Appl. No.: 14/874,372

(22) Filed: Oct. 2, 2015

(65) Prior Publication Data

US 2016/0095743 A1 Apr. 7, 2016

Related U.S. Application Data

(63) Continuation-in-part of application No. 14/506,318, filed on Oct. 3, 2014, now abandoned.

(51) Int. Cl.
*A61F 7/00* (2006.01)
*A61F 7/02* (2006.01)

(52) U.S. Cl.
CPC ........ *A61F 7/02* (2013.01); *A61F 2007/0021* (2013.01); *A61F 2007/022* (2013.01); *A61F 2007/0207* (2013.01); *A61F 2007/0214* (2013.01)

(58) Field of Classification Search
CPC ................ A61F 2007/0021; A61F 7/02; A61F 2007/023
See application file for complete search history.

(56) References Cited

U.S. PATENT DOCUMENTS

| | | | |
|---|---|---|---|
| 1,989,382 A * | 1/1935 | Schnaittacher | A41C 3/04 450/37 |
| 2,298,361 A | 10/1942 | Freund | |
| 4,610,680 A * | 9/1986 | LaFleur | A61F 5/4401 604/385.11 |
| 5,050,595 A * | 9/1991 | Krafft | A61F 7/007 450/38 |
| D324,915 S | 3/1992 | Wastchak | |
| 5,304,215 A | 4/1994 | MacWhinnie et al. | |
| 5,427,563 A | 6/1995 | Manning | |

(Continued)

FOREIGN PATENT DOCUMENTS

| | | |
|---|---|---|
| DE | 4141806 A1 | 5/1993 |
| JP | 2000060889 A | 2/2000 |
| WO | 9414392 | 7/1994 |

*Primary Examiner* — Kaitlyn E Smith
*Assistant Examiner* — Yasamin Ekrami
(74) *Attorney, Agent, or Firm* — Simpson & Simpson, PLLC

(57) ABSTRACT

A thermal device having a waterproof pouch including a first member having a first perimeter and an first waterproof outer surface, and, a second member having a second perimeter and a waterproof second outer surface, wherein the first and second members are partially joined about the first and second perimeter, respectively, and a cavity is formed between the first and second members, a removable insert arranged to be disposed within the cavity, wherein the insert comprises thermal material capable of being heated or cooled, and, a barrier member having an inner surface, wherein the inner surface of the barrier member is releasably secured to the first outer surface of the first member via at least one attachment means.

23 Claims, 12 Drawing Sheets

(56) References Cited

U.S. PATENT DOCUMENTS

| | | | |
|---|---|---|---|
| 5,441,534 A * | 8/1995 | MacWinnie | A61F 7/02 383/901 |
| D365,399 S | 12/1995 | Silver | |
| 5,476,490 A | 12/1995 | Silver | |
| 5,507,794 A * | 4/1996 | Allen | A61F 7/02 126/204 |
| 5,603,653 A * | 2/1997 | Hartman | A41B 9/12 2/267 |
| 5,679,052 A | 10/1997 | Rucki | |
| 5,776,177 A | 7/1998 | MacWhinnie et al. | |
| 5,839,942 A | 11/1998 | Miller | |
| 5,897,580 A * | 4/1999 | Silver | A61F 7/03 128/889 |
| 6,241,715 B1 * | 6/2001 | Houser | A61F 7/02 450/37 |
| 6,261,313 B1 | 7/2001 | MacWhinnie et al. | |
| 6,393,638 B1 | 5/2002 | MacColl | |
| 6,394,879 B1 | 5/2002 | Paige | |
| 6,464,717 B1 | 10/2002 | Smith et al. | |
| D497,996 S | 11/2004 | Rodriguez et al. | |
| 6,916,334 B2 | 7/2005 | Noonan | |
| 7,033,244 B1 | 4/2006 | Barton | |
| 7,081,034 B1 | 7/2006 | Zoellner | |
| 7,179,280 B2 | 2/2007 | Mills | |
| 7,275,977 B1 | 10/2007 | Rhodes | |
| 7,309,275 B1 | 12/2007 | Morales | |
| D571,529 S | 6/2008 | Cook | |
| 7,448,936 B1 | 11/2008 | Kemp-Dorsey | |
| D597,678 S | 8/2009 | Wagner | |
| 8,162,718 B2 | 4/2012 | Chen | |
| 8,167,924 B2 | 5/2012 | Rosenbaum | |
| D673,351 S | 1/2013 | Hill et al. | |
| D702,850 S | 4/2014 | Yockel | |
| 2003/0023291 A1 | 1/2003 | Hanner | |
| 2006/0106355 A1 * | 5/2006 | Bruce | A61F 13/141 604/346 |
| 2006/0154566 A1 | 7/2006 | Nunez et al. | |
| 2007/0067909 A1 | 3/2007 | Lampkins | |
| 2007/0256679 A1 * | 11/2007 | Yim | A61F 7/03 126/263.02 |
| 2009/0138064 A1 * | 5/2009 | Horn | A61F 5/026 607/108 |
| 2009/0222071 A1 | 9/2009 | Li et al. | |
| 2009/0286452 A1 | 11/2009 | Grayson | |
| 2010/0048098 A1 | 2/2010 | Rosario | |
| 2010/0298914 A1 | 11/2010 | Rosenbaum | |
| 2011/0065359 A1 | 3/2011 | Kenny | |
| 2012/0071955 A1 * | 3/2012 | Yockel | A61F 7/02 607/114 |
| 2012/0083863 A1 | 4/2012 | Gillespie | |
| 2012/0090072 A1 | 4/2012 | Oprandi et al. | |
| 2012/0171930 A1 | 7/2012 | Kaufman | |
| 2012/0259303 A1 | 10/2012 | Carter | |
| 2014/0188199 A1 * | 7/2014 | Enderby | A61F 7/08 607/108 |

\* cited by examiner

THERMAL DEVICE FOR TREATING BREASTFEEDING CONDITIONS

CROSS-REFERENCE TO RELATED APPLICATIONS

This application claims priority under 35 U.S.C. § 120 as a continuation-in-part patent application of U.S. patent application Ser. No. 14/506,318, filed Oct. 3, 2014, which application is incorporated herein by reference in its entirety.

FIELD

The present disclosure broadly relates to a device for treating, preventing and relieving breastfeeding conditions, and, more particularly, to a thermal device arranged to be disposed between an inner surface of a bra and a breast of a user.

BACKGROUND

Thermal devices are well known in the art. Both heating and icing, also known as thermotherapy and cryotherapy, respectively, can be effective remedies for treating various ailments. For example, ice is used to calm damaged tissues that are inflamed, red, hot and swollen as inflammation can be incredibly painful and persistent. Ice is commonly used as part of the initial treatment for sprains, strains, and other injuries. In particular, cold slows down blood flow to an injury, thereby reducing pain and swelling. Cryotherapy slows circulation thereby reducing inflammation, muscle spasm, and pain. One problem with icing is that putting the ice pack directly on the skin, using it for long periods, or applying it too often can result in tissue damage, including frostbite.

Heat is used to ease the pain of muscle spasms and trigger points, or conditions that are often dominated by them, like back and neck pain. Heat is generally recommended for chronic aches and pains, or new and minor muscular pains. Muscles tend to relax under thermotherapy as the heat can help improve circulation, reduce muscle spasms, and increase range of motion. In particular, heat opens up blood vessels, which increases blood flow and supplies oxygen and nutrients to reduce pain in joints and relax sore muscles, ligaments, and tendons. One problem with heating is that too much heat can harm skin and damage tissue.

During breastfeeding, several types of complications can arise, many of which can be at least partially relieved with either heating or icing. Some of the complications include sore or cracked nipples, painful lumps resulting from a clogged milk duct, mastitis that can result in infection, yeast infections, engorged breasts, etc. Some conditions, such as clogged milk ducts, can be treated with heat to unplug the ducts, whereas other conditions, such as engorged breasts, can be treated by icing to reduce the swelling and allow the ducts to open.

One thermal device, disclosed in U.S. Pat. No. 5,441,534 (MacWinnie et al.), includes a thermal heat pack for heating the female breast during nursing to reduce swelling and irritation. The thermal heat pack has an inner cavity for a heat conductive gel and a cloth layer stitched to a member. One problem with the thermal heat pack disclosed by MacWinnie et al. is that the thermal heat pack is only able to be heated and not cooled, which results in certain breastfeeding conditions not being able to be treated. Another problem is that the cloth layer is stitched to the member, and thus, the cloth layer is not removable, which can result in unsanitary conditions and infection. Yet another problem is that the thermal heat pack lacks any type of attachment means for securing the device to a bra, which can result in the thermal heat pack becoming dislodged during use. Another problem with the thermal heat pack is that the thermal element is not removable, and thus, cannot be heated separately.

Another thermal device, disclosed in U.S. Pat. No. 5,507,794 (Allen), includes an elongated support member having two ends, an adjustable securing member for removably securing the support member ends, at least one breast pouch disposed on the support member, a positioning member for removably positioning the breast pouch, and a temperature regulator positioned in the breast pouch for imparting a predetermined temperature to the wearer's breast regions to relieve the discomforts of swelling and tenderness thereof.

However, for a nursing mother, many problems arise if milk leaks from the nipple of her breast while using the thermal device disclosed by Allen. For example, a nursing mother is required to wash the entire removable breast pouch and/or support member if excess milk leaks from the nipple of her breast and onto the thermal device. Further, Allen's device does not prevent excess milk from leaking through the breast pouch and onto a bra, outer clothing, and/or material contacting the breast pouch, such as a bed sheet.

United States Patent Application No. 2012/0090072 (Oprandi et al.) discloses a hospital garment with adjustable pockets. The pockets have an inner chamber lined with waterproof material (i.e., plastic) to prevent condensation or other wetness from the hot/cold therapy packs from seeping through to the skin of the patient. Even though the inner chamber lined with waterproof material may prevent wetness from seeping out of the inner chamber, it does not prevent wetness applied to the rear outer surface of the pocket from seeping to the front outer surface of the pocket. In other words, the configuration disclosed by Oprandi et al. enables the front absorbent outer surface of the pocket to absorb any liquid absorbed by the rear absorbent outer surface of the pocket because both outer surfaces are absorbent and in contact with each other with no intervening hydrophobic material. This is a problem for nursing mothers because excess leakage of milk will seep around to the front of the pouch and onto outer clothing.

Thus, there is a long-felt need for a thermal device where the thermal element does not directly contact the skin to prevent damage to the skin and surrounding tissue. There is also a long-felt need for a thermal device that can be used for both heating and cooling the breast. Additionally, there is a long-felt need for a thermal device, having a pouch with a removable thermal insert that can be heated separately. Also, there is a long-felt need for a thermal device that prevents liquid from seeping from the rear of the device to the front of the device. Furthermore, there is a long-felt need for a thermal device having a barrier member removably secured to the pouch, such that the barrier member, which contacts the breast, is washable to prevent possible infections and can be soaked to provide moist heat therapy or gentle cooling therapy.

BRIEF SUMMARY

According to aspects illustrated herein, there is provided a thermal device having a pouch including: a first member having a first perimeter and a waterproof first outer surface, a second member having a second perimeter and a waterproof second outer surface where the first and second members are partially joined about the first and second perimeters, respectively; a cavity formed between the first and second members; a removable insert arranged to be disposed within the cavity, the insert including: an insert outer surface, an insert inner surface, and a thermal material encapsulated within the insert inner surface and capable of being heated or cooled; and a barrier member having an inner surface; wherein the inner surface of the barrier member is releasably securable to the first outer surface of the first member via at least one attachment means.

According to aspects illustrated herein, there is provided a thermal device arranged to be disposed between an article of clothing and an area of skin, the thermal device including a pouch including: a first member having a first perimeter and a first outer surface arranged to face the article of clothing wherein the first outer surface is hydrophobic, and a second member having a second perimeter and a second outer surface, wherein the first and second members are partially joined about the first and second perimeters, respectively, and a cavity is formed between the first and second members, a removable insert arranged to be disposed within the cavity, wherein the insert comprises thermal material capable of being heated or cooled, and a waterproofing member having an inner surface and a third outer surface. The inner surface is releasably securable to the first outer surface of the first member via at least one attachment means.

According to aspects illustrated herein, there is provided a thermal device including: a first member having a first perimeter and a first outer surface made of a first material, a second member having a second perimeter and a second outer surface made of a second material, wherein the second material is different than the first material and wherein the first and second members are joined about the first and second perimeters, respectively, and form a chamber therebetween, and a thermal material capable of being heated or cooled disposed within the chamber.

A general object is to provide a thermal device that can be worn with or without a bra.

Another object is to provide a thermal device that protects clothing from any leaking water or milk.

Another object is to provide a thermal device that has the option to provide moisture to the skin.

Another object is to provide a thermal device that can be placed anywhere on the body.

In one embodiment, the means for securing the thermal device to a bra is a strap, which includes a first end secured to a first member and a second end secured to a second member, where the bra has a strap and the strap of the thermal device is removably secured to the strap of the bra. Additionally, the first end of the strap further comprises at least one attachment means for securing the first end of the strap to the first member. Preferably, the at least one attachment means is a snap fastener. However, it should be appreciated that the attachment means can be any suitable means known in the art, such as a snap fastener, hook and loop fastener, removable adhesive, magnets, etc.

Preferably, the portions of the first edge and the second edge are at least partially connected via stitching. However, it should be appreciated that the first edge and the second edge can be secured to one another by any suitable means such as stitching, hook and loop fastener, adhesive, magnets, heat-sealing, etc. Preferably, a barrier member is removably secured to the first member and the attachment means for securing the inner surface of the barrier member to the outer surface of the first member includes a hook and loop fastener. However, it should be appreciated that the barrier member can be secured to the first member by any suitable means known in the art, such as hook and loop fastener, removable adhesive, magnets, a snap fastener, etc.

In an embodiment, the pouch is made of a waterproof material, such as a fabric laminated with polyurethane, configured on the outside surface of the pouch closest to the bra or clothing. In contrast, the barrier member is made of an absorbent material, such as an absorbent cloth. However, it should be appreciated that any of the components, such as the pouch, the barrier member, the strap, etc., can be made of any suitable material known in the art.

In an embodiment, the pouch is made of absorbent material and a waterproofing member is provided.

In an embodiment, the thermal device includes a first member made of absorbent material stitched to a second member made of a waterproof material.

In one embodiment, the first member has a first perimeter, P1, the second member has a second perimeter, P2, the barrier member has a third perimeter, P3, and the insert has a fourth perimeter, P4. Preferably, the length of the first perimeter, P1, the length of the second perimeter, P2, and the length of the third perimeter, P3, are substantially the same. The length of the fourth perimeter, P4, is less than the lengths of the first perimeter, P1, and the second perimeter, P2. Additionally, the first member, the second member, and the barrier member are substantially circular in shape. However, it should be appreciated that any of the elements of the thermal device can vary in size, shape, and configuration.

In another embodiment, the pouch is formed from a single piece of material. Thus, the portion of the first edge and the portion of the second edge are at least partially integral with one another.

These and other objects, advantages and features of the various embodiments will be better appreciated by those having ordinary skill in the art in view of the following detailed description in view of the drawings.

BRIEF DESCRIPTION OF THE DRAWINGS

The nature and mode of operation of the various embodiments will now be more fully described in the following detailed description taken with the accompanying drawing figures, in which.

DETAILED DESCRIPTION

At the outset, it should be appreciated that like drawing numbers on different drawing views identify identical, or functionally similar, structural root elements of the various embodiments described. Moreover, although any methods, devices or materials similar or equivalent to those described herein can be used in the practice or testing of these embodiments, some embodiments of methods, devices, and materials are now described.

Furthermore, it is understood that this disclosure is not limited to the particular methodology, materials and modifications described and, as such, may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be appreciated that the term "substantially" is synonymous with terms such as "nearly", "very nearly", "about", "approximately", "around", "bordering on", "close to", "essentially", "in the neighborhood of", "in the vicinity of", etc., and such terms may be used interchangeably as appearing in the specification and claims. Additionally, the term "thermal" is defined as "being or involving a state of matter dependent upon temperature," and thus, may be used interchangeably with reference to an element that can be "heated" or "cooled," as appearing in the specification and claims. Any methods, devices or materials similar or equivalent to those described herein can be used in the practice or testing of the example embodiments.

Figure 1:
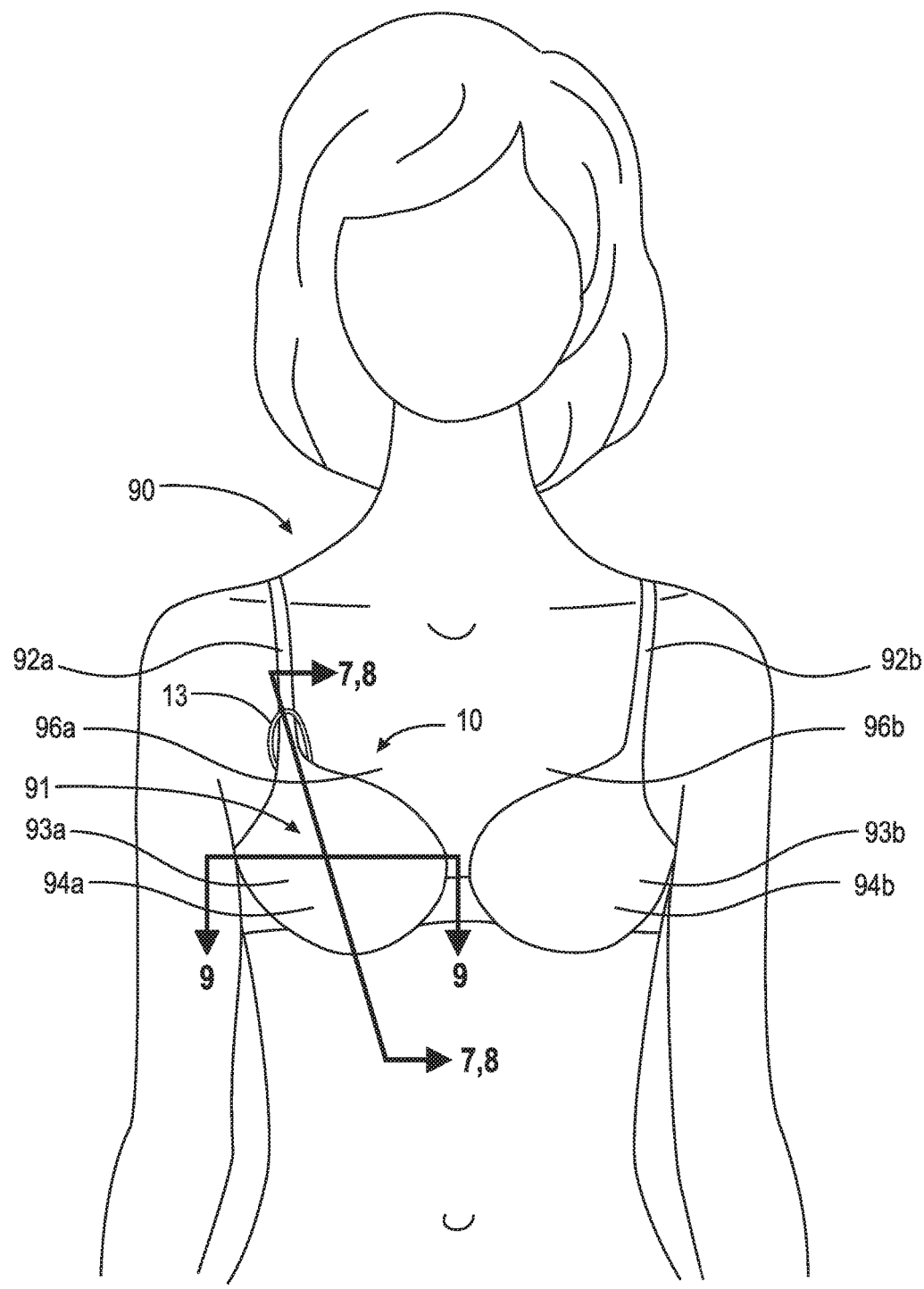
FIG. 1 is a view of a thermal device, shown worn by a user where the thermal device is connected to a bra.

Adverting now to the figures, FIG. 1 is a view of user 90 wearing bra 91, wherein device 10 is hidden from view behind bra cup 93a. User 90 has breasts 96a, 96b, and is shown wearing bra 91, which includes bra straps 92a, 92b, and bra cups 93a, 93b. Bra cup 93a includes cup outer surface 94a and cup inner surface 95a (shown in FIG. 2). Similarly, bra cup 93b includes cup outer surface 94b and cup inner surface 95b (shown in FIG. 2). Device 10 is disposed between cup inner surface 95a and breast 96a.

Figure 2:
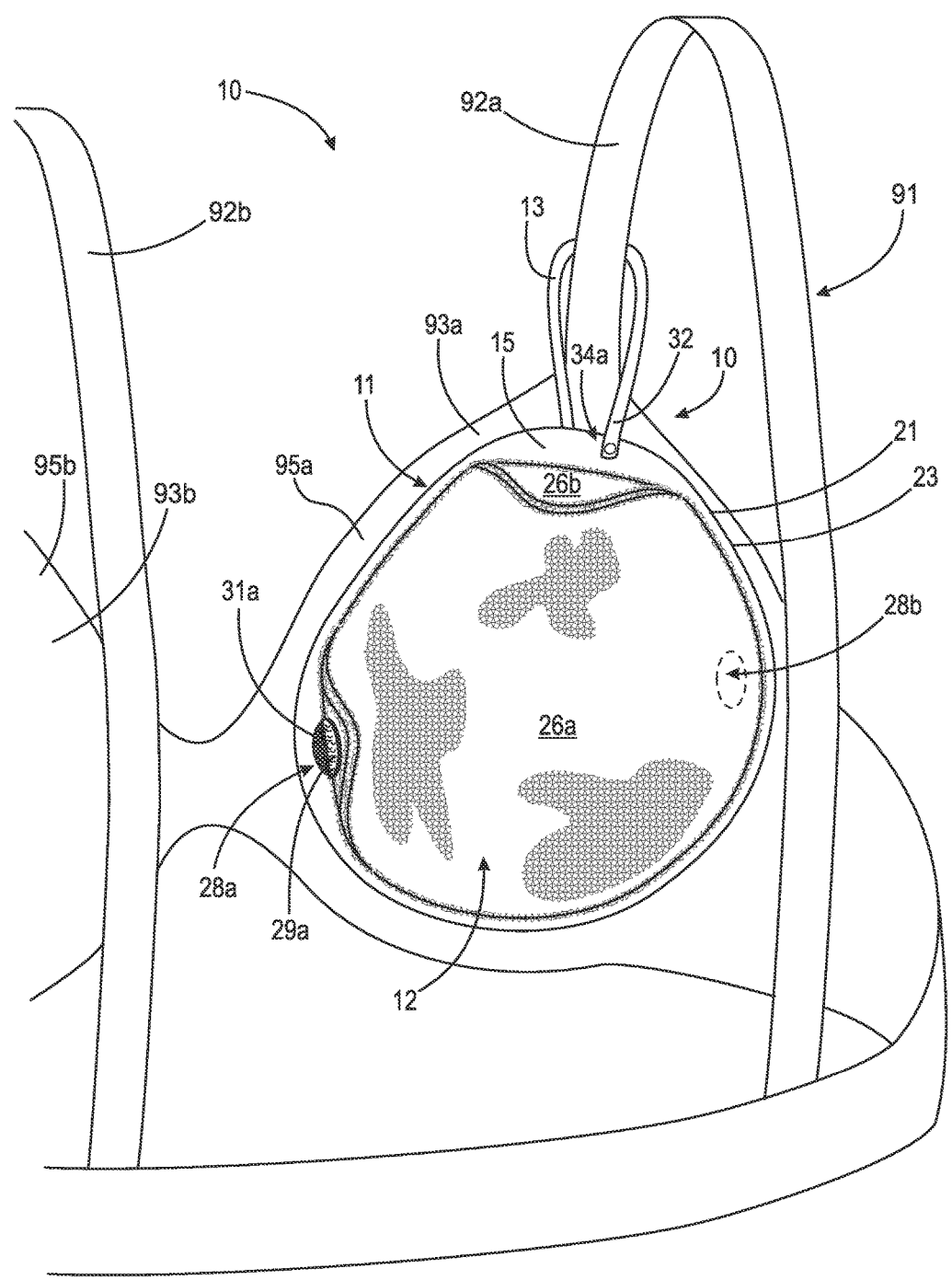
FIG. 2 is a rear view of the thermal device shown in FIG. 1.

FIG. 2 is a rear elevational view of device 10, shown worn by a user where the thermal device is secured to bra 91.

Figure 3:
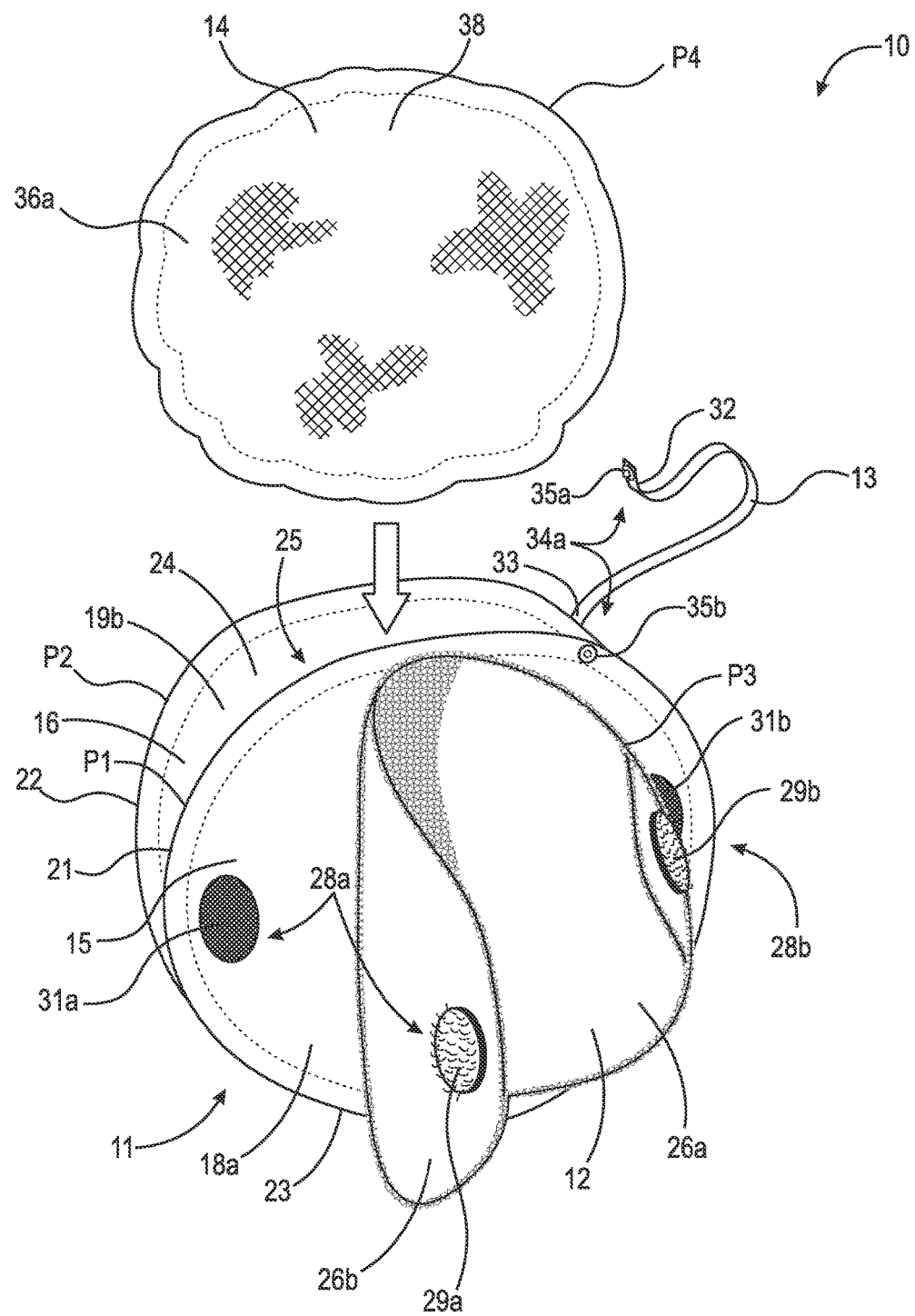
FIG. 3 is a partially exploded view of the thermal device.

FIG. 3 is an exploded view of device 10.

Figure 4:
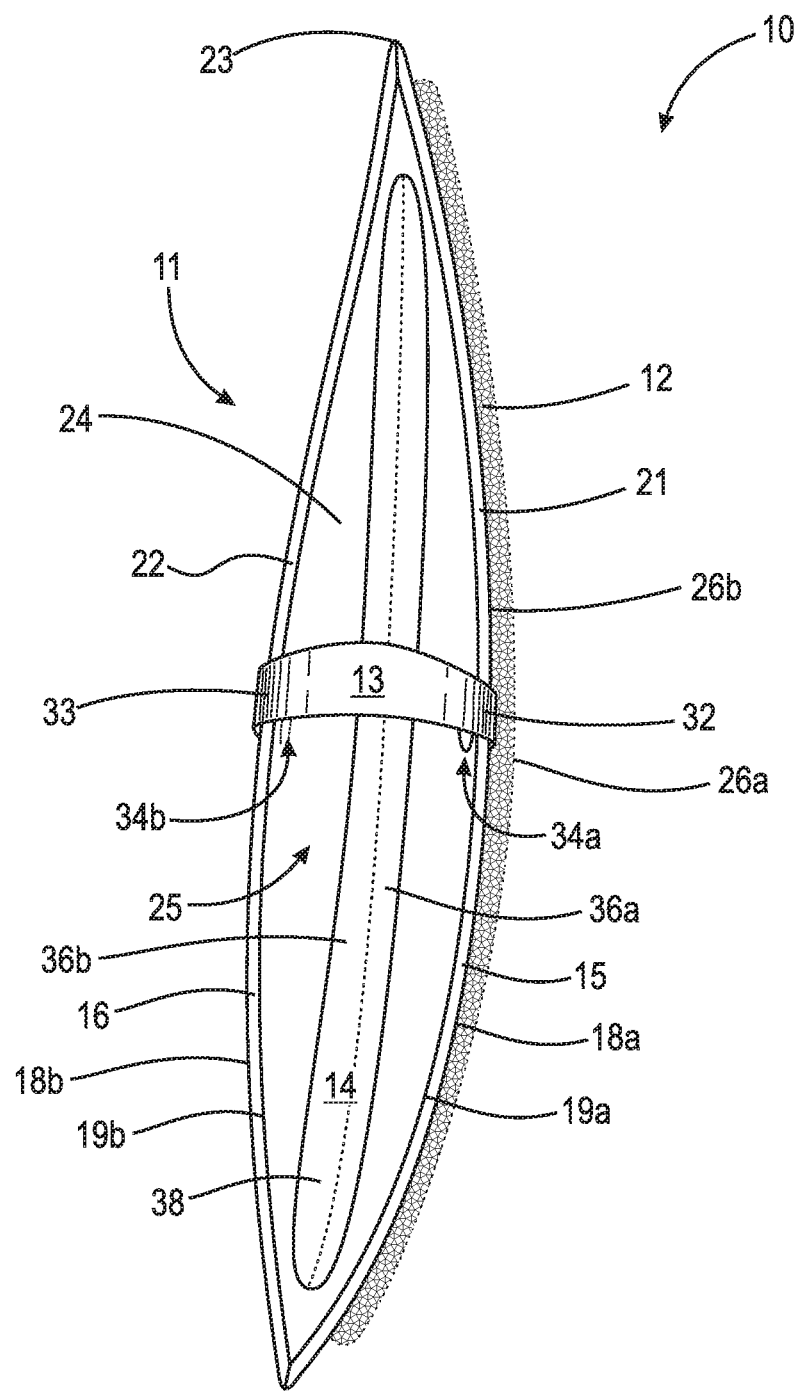
FIG. 4 is a top view of the thermal device.

FIG. 4 is a top view of device 10.

Figure 5:
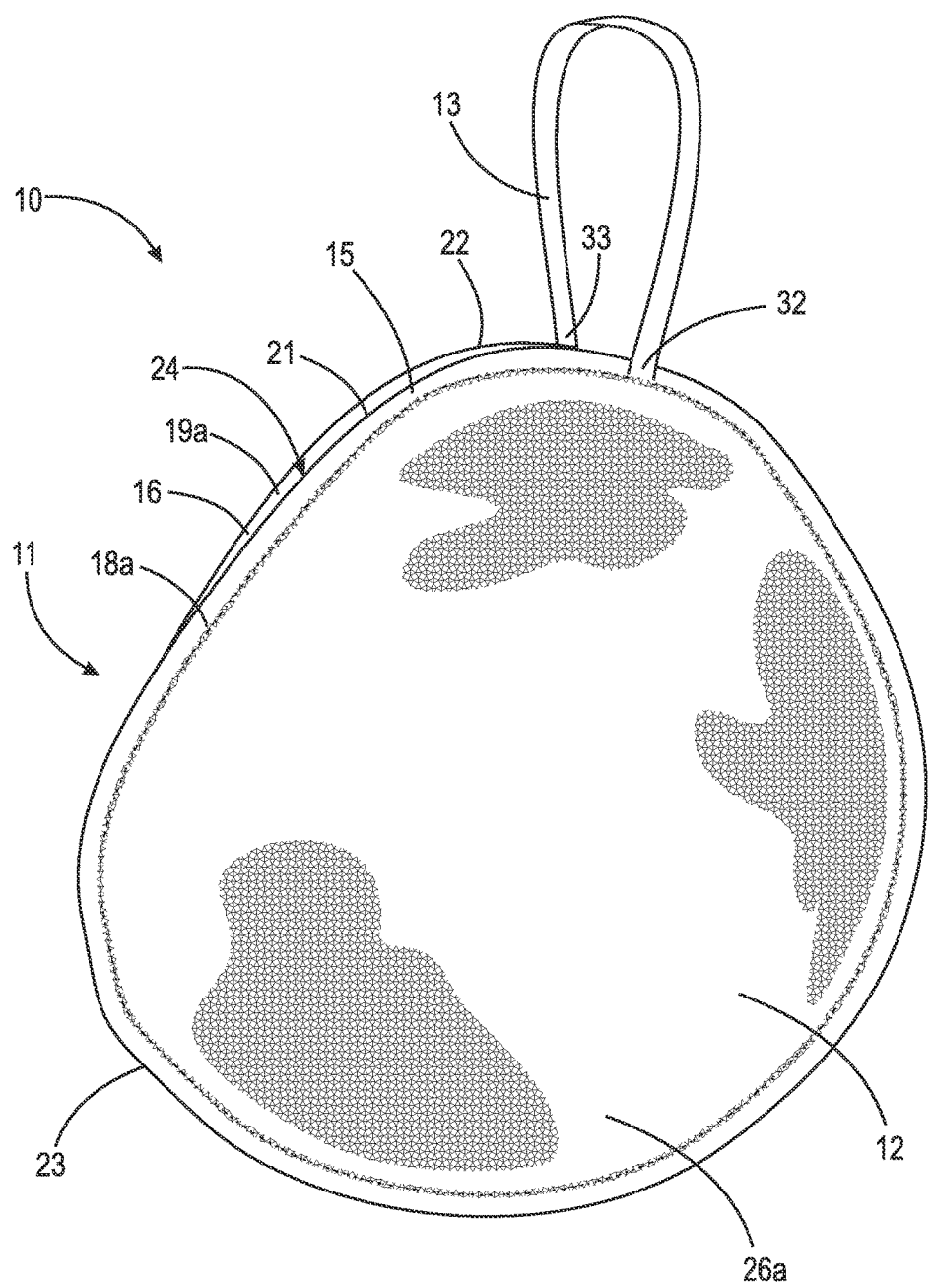
FIG. 5 is a rear view of the thermal device.

FIG. 5 is a rear view of device 10.

Figure 6:
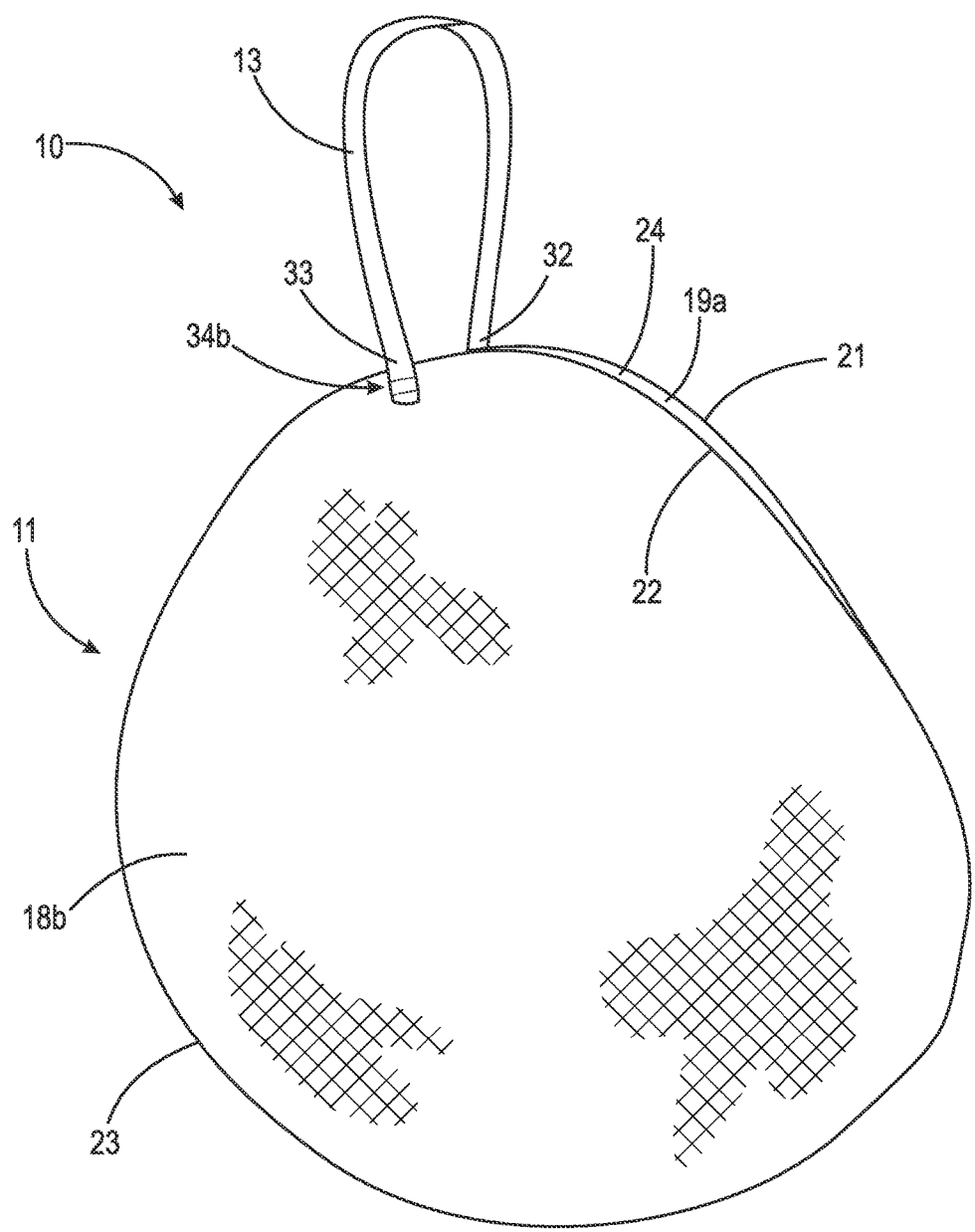
FIG. 6 is a front view of the thermal device.

FIG. 6 is a front view of device 10.

Figure 7:
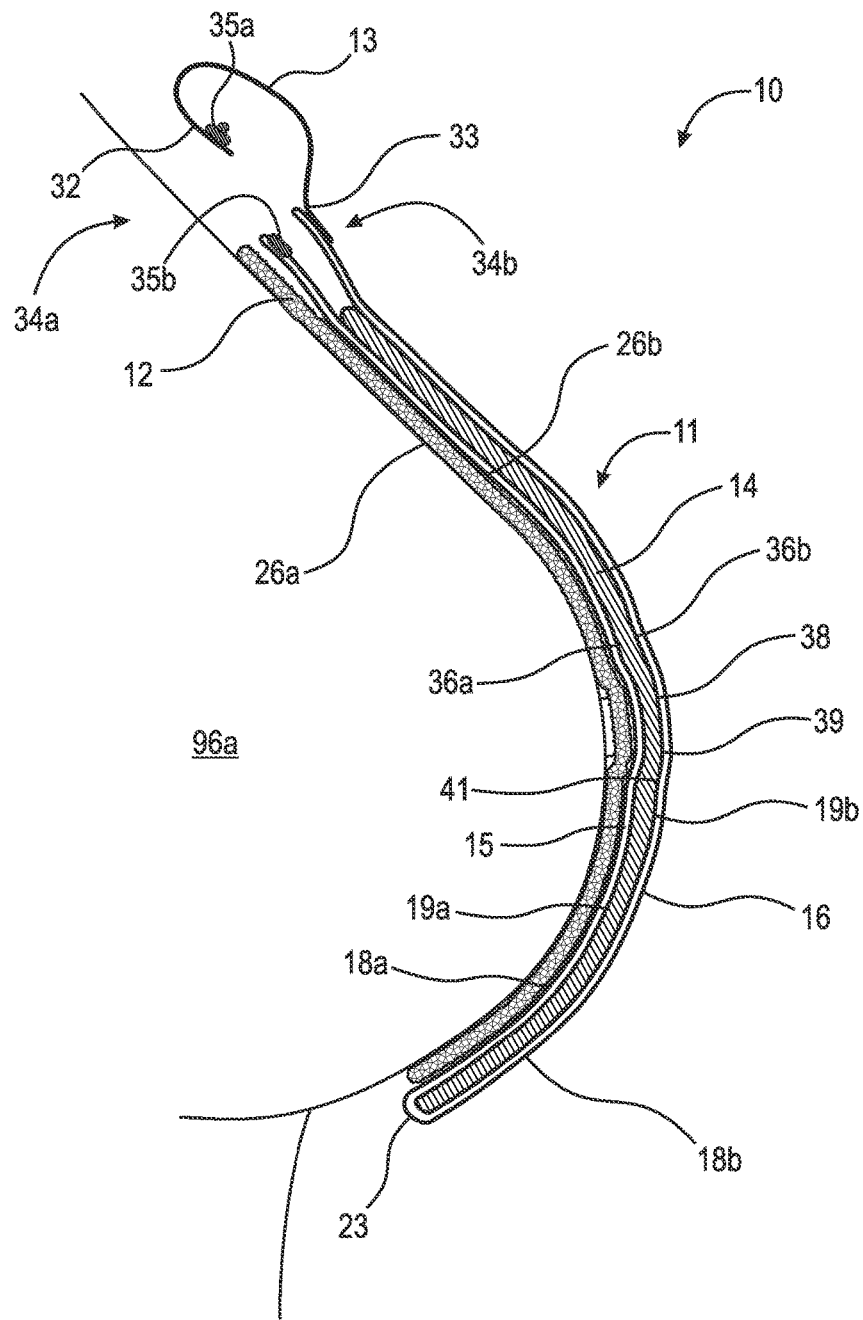
FIG. 7 is a cross-sectional view of the thermal device, taken generally along line 7-7 of FIG. 1.
Figure 8:
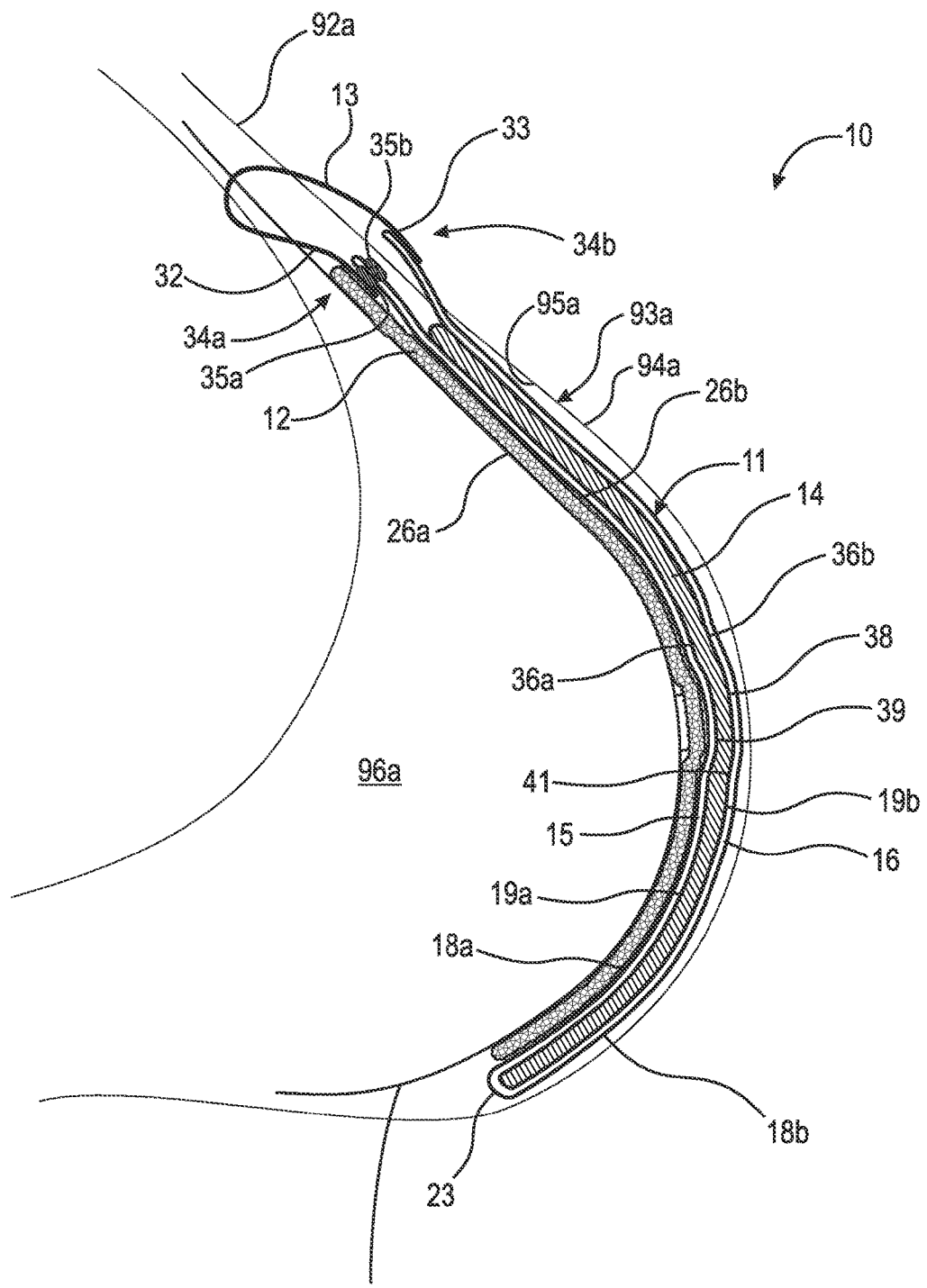
FIG. 8 is a cross-sectional view of the thermal device, taken generally along line 8-8 of FIG. 1.
Figure 9:
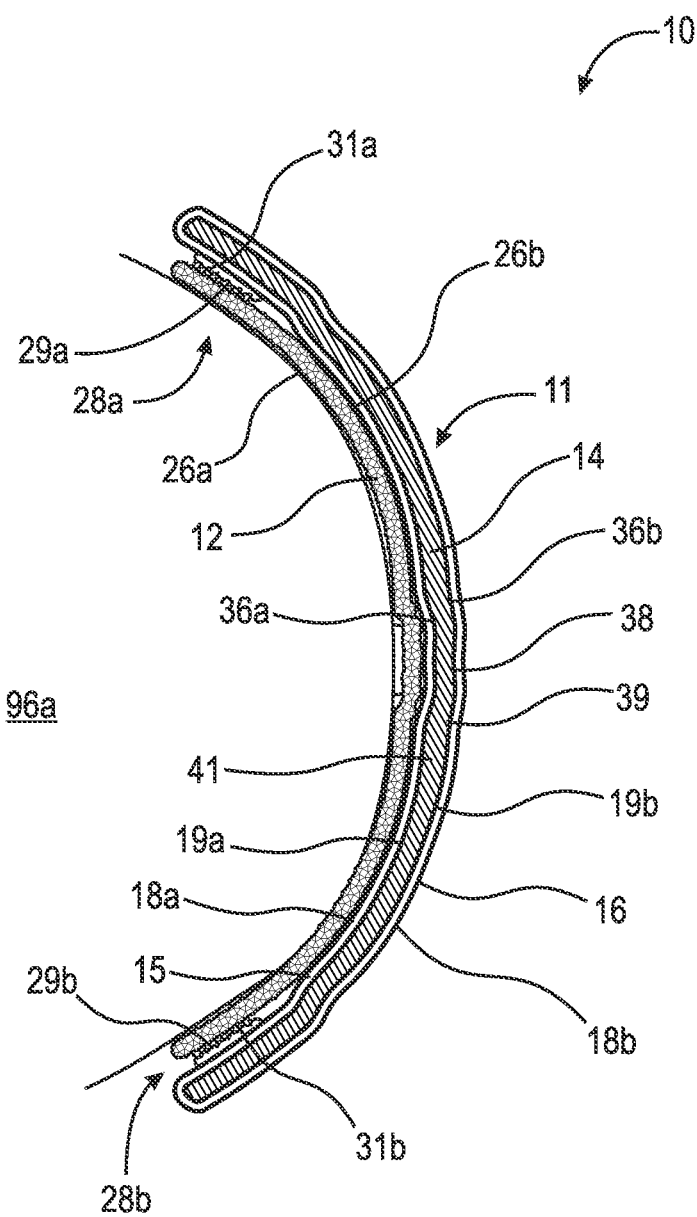
FIG. 9 is a cross-sectional view of the thermal device, taken generally along line 9-9 of FIG. 1.

FIGS. 7 through 9 are various cross-sectional views of device 10. FIGS. 7 and 9 are shown with bra 91 removed and FIG. 8 is shown with bra 91.

The following should be viewed in light of FIGS. 1 through 9. Device 10 generally includes pouch 11, cavity 25, insert 14, barrier member 12, and strap 13. Pouch 11 includes member 15 having edge 21, outer surface 18a, and inner surface 19a and member 16 having edge 22, outer surface 18b, and inner surface 19b.

As shown in FIG. 2, outer surface 18b (shown in FIG. 4) of member 16 (shown in FIG. 3) contacts cup inner surface 95a of bra cup 93a. As pouch 11 is preferably made of a flexible material, pouch 11 conforms to the curvature of bra cup 93a, which holds device 10 in place and prevents shifting of device 10 while in use. Additionally, in the event that device 10 is dislodged from bra cup 93a, strap 13 provides a further means of securing device 10 to bra 91. In particular, strap 13 is looped around bra strap 92a and removably secured to pouch 11 via attachment means 34a. It should be appreciated that while the various figures depict a single thermal device 10, a plurality of thermal devices may be used. For example, device 10 may also be disposed between bra cup 93b and breast 96b (shown in FIG. 1). Similarly, outer surface 18b (shown in FIG. 4) of member 16 (shown in FIG. 4) can contact cup inner surface 95b of bra cup 93b and pouch 11 can conform to the curvature of bra cup 93b.

Moreover, barrier member 12 has barrier outer surface 26a and barrier inner surface 26b. Barrier inner surface 26b is secured to outer surface 18a (shown in FIG. 3) of member 15 via at least one attachment means 28a, 28b. Preferably, barrier inner surface 26b of barrier member 12 is removably secured to outer surface 18a (shown in FIG. 3) of member 15 by attachment means 28a, 28b. Preferably, attachment means 28a includes hook portion 29a and loop portion 31a, where hook portion 29a is disposed on barrier inner surface 26b and engages loop portion 31a disposed on outer surface 18a. Similarly, attachment means 28b includes hook portion 29b and loop portion 31b, where hook portion 29b is disposed on barrier inner surface 26b and engages loop portion 31b disposed on outer surface 18a. Preferably, barrier member 12 is removable, which is important for sanitary purposes since barrier member 12 directly contacts the breasts 96a, 96b. Furthermore, barrier member 12 is disposable or washable to prevent infections caused by mastitis, thrush, etc. However, it should be appreciated that barrier member 12 can be secured to member 15 by any suitable means known in the art, such as hook and loop fastener, removable adhesive, magnets, a snap fastener, etc. Additionally, barrier member 12 is made of an absorbent material, such as an absorbent cloth. Milk tends to leak from the nipple of the breast during breastfeeding, and thus, it is pertinent that barrier member 12 absorbs excess milk. Moreover, barrier member 12 can be soaked in a liquid prior to being secured to pouch 11 in order to provide moist heat therapy. However, it should be appreciated that barrier member 12 can be made of any suitable absorbent material known in the art.

As shown in FIG. 3, edge 21 and edge 22 are adjacent to one another. A portion of edge 21 and a portion of edge 22 are at least partially connected to one another, forming pouch edge 23. Preferably, the portions of edge 21 and edge 22 are at least partially connected via stitching. However, it should be appreciated that edge 21 and edge 22 can be secured to one another by any suitable means such as stitching, hook and loop fastener, adhesive, heat-sealing, magnets, etc. Conversely, a portion of edge 21 and portion of edge 22 is also at least partially detached from one another, which is necessary to form opening 24. Member 15 and member 16 at least partially enclose cavity 25. In another embodiment, pouch 11 is formed from a single piece of material. Thus, the portion of edge 21 and the portion of edge 22 are at least partially integral with one another. Preferably, pouch 11 is made of a waterproof material, such as a fabric laminated with polyurethane. However, it should be appreciated that pouch 11 can be made of any suitable material known in the art that enables at least the outer surface of pouch 11 to be waterproof.

When in use, insert 14 is placed through opening 24 and is disposed within cavity 25. Insert 14 includes insert outer surface 36a, insert outer surface 36b (shown in FIG. 4), insert inner surface 38, and is filled with thermal material 39 (shown in FIG. 7). When insert 14 is disposed within cavity 25, insert outer surface 36a and insert outer surface 36b (shown in FIG. 4) contacts inner surface 19a of member 15 and inner surface 19b (shown in FIG. 4) of member 16, respectively. Preferably, thermal material 39 is flexible and can be primarily liquid or primarily solid in nature, and which, due to its flexibility, can be adapted to conform to any sized contour of the breast. Heat retentive and conductive materials are conventional and are well known in the art of thermal pack appliances. For example, thermal material 39 may be made of silica gel, ceramic beads, glass beads, vinyl-based synthetic beads, sodium acetate, sodium polyacrylate, hydroxyethyl cellulose, paraffin, rice, flax seed, barley, corn, buckwheat, etc. In another embodiment, insert 14 is not filled with thermal material 39 and is instead itself made of thermal material 39 capable of being heated or cooled. However, it should be appreciated that thermal material 39 can be made of any suitable material that is capable of being heated or cooled known in the art.

When in use, user 90 (shown in FIG. 1) removes insert 14 from pouch 11 and uses a heating or cooling apparatus, such as a microwave, freezer, refrigerator, etc., to heat or cool thermal material 39 (shown in FIG. 7). However, a heating or cooling apparatus is not required if insert 14 is composed of chemicals that initiate a chemical reaction that results in a temperature change of insert 14. Then, insert 14 is placed in opening 24 and disposed within cavity 25.

FIG. 8 shows device 10 disposed between bra cup 93*a* and breast 96*a*. Device 10 adjusts and conforms to the contours of various sized female breasts to therapeutically heat or cool adjacent skin areas of the breast. It is important that thermal material 39 does not directly contact the skin of user 90 (shown in FIG. 1) after it is heated or cooled before applying it to the breast so that it does not damage the surrounding tissue. Additionally, strap 13 is looped around bra strap 92*a* and secured via strap attachment means 34*a*.

As shown in the various figures, the means for securing device 10 to bra 91 is strap 13, which includes end 32 secured to member 15 and end 33 secured to member 16. As mentioned above, strap 13 is removably secured to bra strap 92*a*. End 32 includes strap attachment means 34*a* for securing end 32 of strap 13 to member 15. Similarly, end 33 includes strap attachment means 34*b* for securing end 33 of strap 13 to member 16. Preferably, strap attachment means 34*a* removably secures end 32 to member 15, while strap attachment means 34*b* fixedly secures end 33 to member 16. Preferably, strap attachment means 34*a* is a snap fastener and includes male part 35*a* and female part 35*b*, which engage one another to secure device 10 once strap 13 is looped around bra strap 92*a*. Conversely, strap attachment means 34*b* fixedly secures end 33 to member 16 via stitching. In another embodiment, strap attachment means 34*b* may also removably secure end 33 to member 16 in order for strap 13 to be completely removable from pouch 11. However, it should be appreciated that attachment means 34*a*, 34*b* can be any suitable means known in the art, such as a snap fastener, hook and loop fastener, removable adhesive, magnets, etc.

In one embodiment, member 15 includes perimeter P1, member 16 includes perimeter P2, barrier member 12 includes perimeter P3, and insert 14 includes perimeter P4. Preferably, the length of perimeter P1, the length of perimeter P2, and the length of perimeter P3, are substantially the same. The length of perimeter P4, is less than the lengths of perimeter P1 and perimeter P2. It is important for the length of perimeter P4, to be less than the lengths of the perimeters P1, P2, in order for insert 14 to fit within pouch 11. Preferably, member 15, member 16, barrier member 12, and insert 14 are substantially circular in shape. However, it should be appreciated that any of these elements can vary in size, shape, and configuration.

Figure 10:
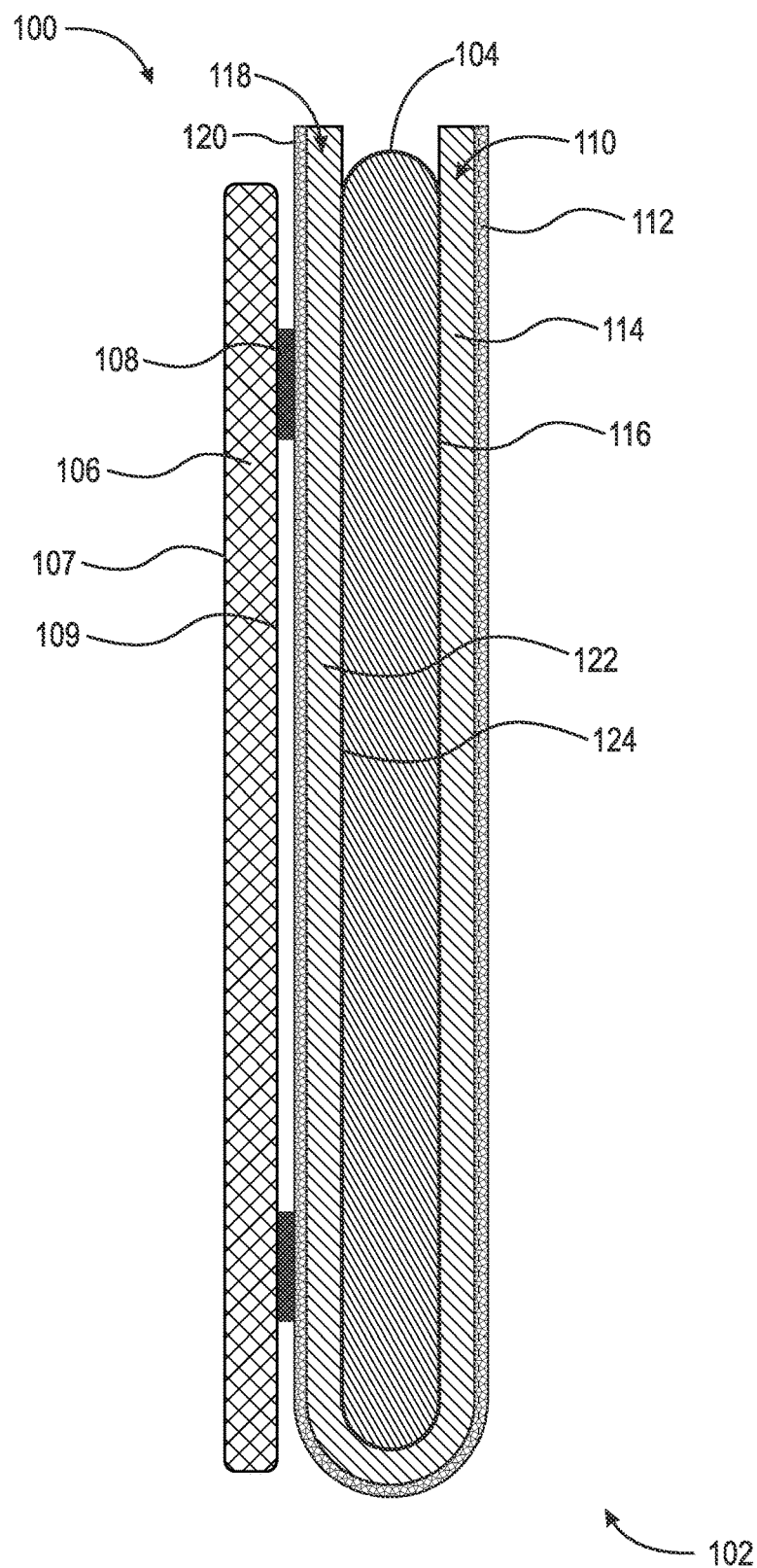
FIG. 10 is a cross-sectional view of an example embodiment of a thermal device.

FIG. 10 is a cross-sectional view of thermal device 100. Thermal device 100 includes pouch 102 including insert 104 disposed therein, and absorbent member 106 releasably secured to pouch 102 by hook and loop fasteners 108. Absorbent member 106 includes outer surface 107 configured to contact skin of a patient, and front surface 109 to contact pouch 102 via hook and loop fasteners 108.

Pouch 102 includes front member 110 and rear member 118. Rear member 118 is secured to absorbent member 106 via hook and loop fasteners 108. Front member 110 is shown as a continuous piece of the same material as rear member 118, however front member 110 can be a separate piece of material stitched together with rear member 118. In an example embodiment, front member 110 is made of fabric 114 and includes polyurethane laminate 112 on the outer surface of front member 110. Pouch 102 is waterproof due to polyurethane laminate 112 lining the outer surface of the pouch. Preferably, inner surface 116 of front member 110 is absorbent. Similarly, in an example embodiment where front member 110 is a separate piece of material than rear member 118, rear member 118 is made of fabric 122 and includes polyurethane laminate 120 on the outer surface of the rear member. Preferably, inner surface 124 of rear member 118 is absorbent. Inner surface 116 of the front member and inner surface 124 of the rear member create a cavity to hold insert 104.

Figure 11:
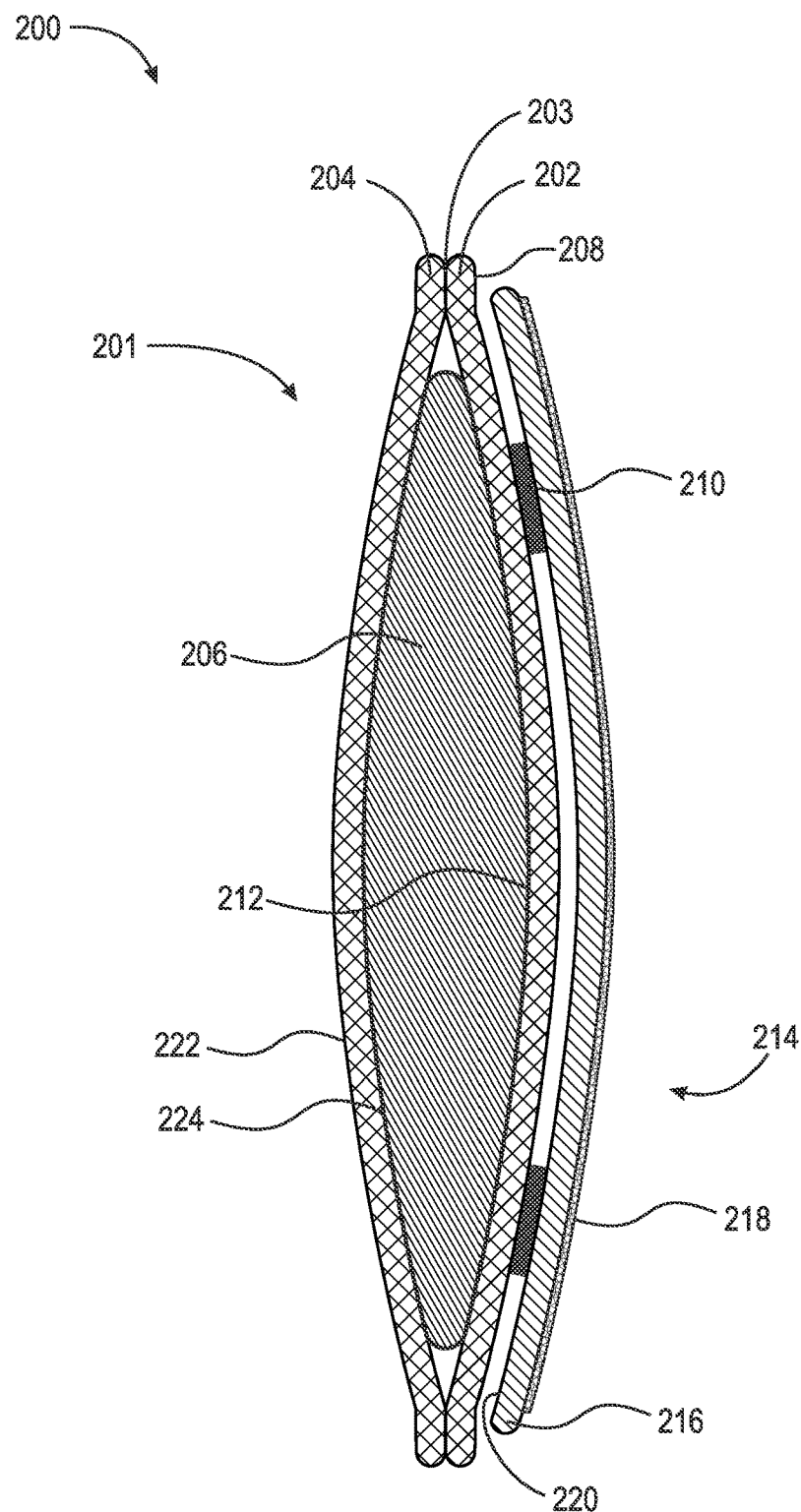
FIG. 11 is a cross-sectional view of an example embodiment of a thermal device; and, FIG. 12 is a cross-sectional view of an example embodiment of a thermal device.

FIG. 11 is a cross-sectional view of thermal device 200. Thermal device 200 includes pouch 201 made from absorbent front member 202 and absorbent rear member 204, insert 206 disposed within pouch 201, and waterproof member 214 releasably secured to pouch 201 by hook and loop fasteners 210. In an embodiment, fasteners 210 are hook fasteners only and secured to pouch 201, wherein the material of member 214 interacts with the hook fasteners to secure member 214 to pouch 201.

Pouch 201 includes front member 202 and rear member 204. Rear member 204 is configured to contact skin of a patient, and front member 202 is configured to be secured to waterproof member 214 via hook and loop fasteners 210. Front member 202 is shown as a separate piece of material secured to rear member 204 via stitching, however, it should be appreciated that front member 202 can be made of the same continuous piece of material as rear member 204, or that heat-sealing is used instead of stitching. Preferably, thermal device 200 includes front member 202, rear member 204 made of absorbent material, insert 206 disposed between inner surfaces 212 and 224 of front member 202 and rear member 204, respectively, and removable member 214, which is made of waterproof material. Pouch 201 can also be embodied as a pillow in that front member 202 and rear member 204 are sewn together to form a chamber such that insert 206 is completely encased by front member 202 and rear member 204. The chamber is enclosed via stitching 203. However, it should be appreciated that front member 202 and rear member 204 may be sealed by any suitable means such as hook and loop fastener, adhesive, heat-sealing, magnets, etc.

Member 214 is secured to front surface 208 of pouch 201 via hook and loop fasteners 210 disposed on inner surface 220 of the member 214. Member 214 provides a waterproof barrier between front member 202 and rear member 204 and any outer clothing or a bra. This prevents liquid from outer surface 208 and outer surface 222 from seeping through pouch 201 onto cup inner surface 95*a*. Preferably, member 214 is made of fabric 216 and includes polyurethane laminate 218 on the outer surface. Thermal device 200 is waterproof due to laminate 218 lining the outer surface of member 214. In an example embodiment, front member 202 is waterproof as well as member 214, while rear member 202 is absorbent.

Figure 12:
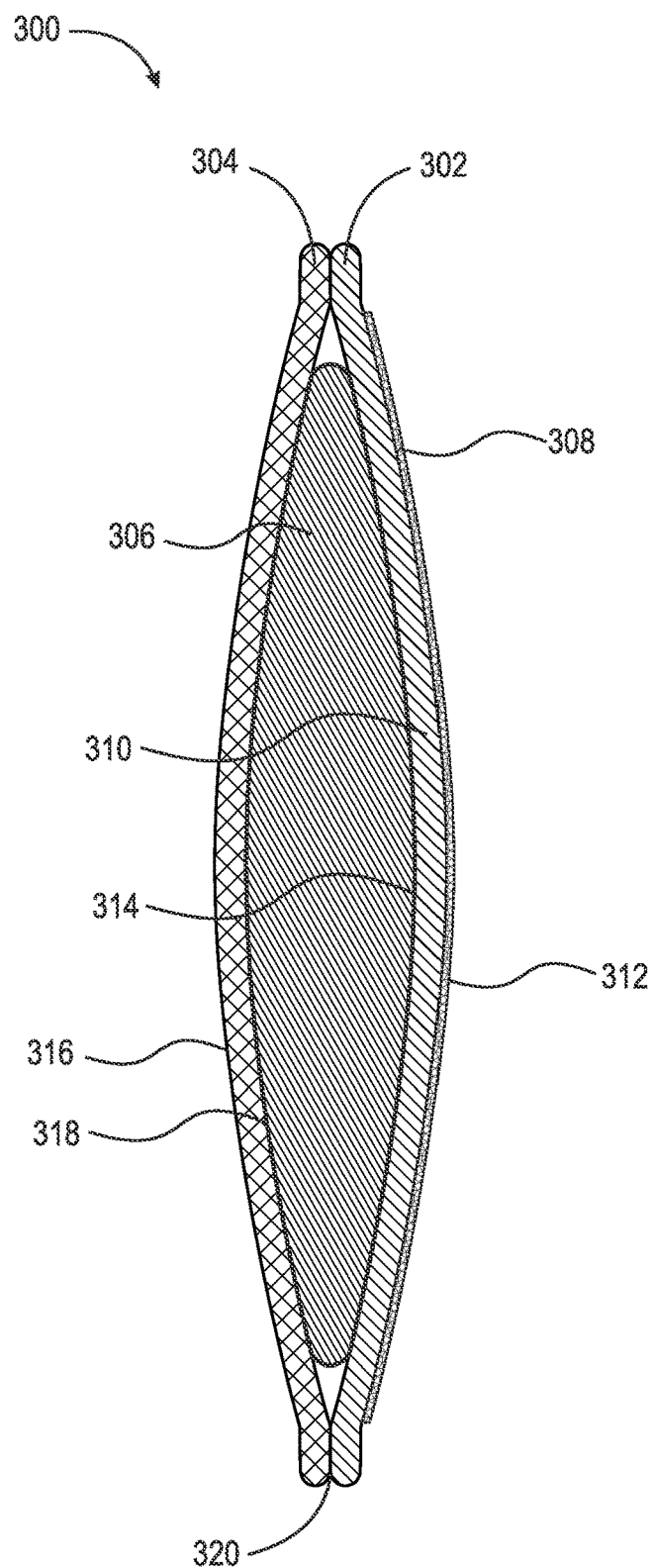

FIG. 12 is a cross-sectional view of thermal device 300. Thermal device 300 is a pillow having front member 302 secured to rear member 304 and completely encasing thermal material 306 in a chamber between front member 302 and rear member 304. Outer surface 308 of front member 302 is waterproof. Preferably, front member 302 is made of fabric 310 with waterproof laminate 312 lining the outer surface of front member 302. This prevents liquid from outer surface 308 from seeping through thermal device 300 directly onto cup inner surface 95a. Preferably, inner surface 314 of front member 302 is absorbent. Rear member 304 includes outer surface 316 configured to contact skin of a patient and inner surface 318. Inner surface 314 and inner surface 318 of front member 302 and rear member 304, respectively, create a chamber for thermal material 306. The chamber is enclosed via stitching 320. However, it should be appreciated that front member 302 and rear member 304 may be sealed by any suitable means such as hook and loop fastener, adhesive, heat-sealing, magnets, etc. In an example embodiment, inner surface 318 of rear member 304 includes a waterproof lining or laminate in order to protect thermal material 306 from moisture provided to outer surface 316 such as any milk that may have leaked from the nipple of a nursing mother. Waterproof layer 312 preferably lines the entirety of outer surface 308.

Thus, it is seen that the objects of the example embodiments are efficiently obtained, although modifications and changes should be readily apparent to those having ordinary skill in the art, which modifications are intended to be within the spirit and scope of the claims. It also is understood that the foregoing description is illustrative and should not be considered as limiting. Therefore, other embodiments are possible without departing from the spirit and scope of the claims.

LIST OF REFERENCE NUMBERS

10 Device
11 Pouch
12 Barrier member
13 Strap
14 Insert
15 Member
16 Member
18a Outer surface
18b Outer surface
19a Inner surface
19b Inner surface
21 Edge
22 Edge
23 Pouch edge
24 Opening
25 Cavity
26a Barrier outer surface
26b Barrier inner surface
28a Attachment means
28b Attachment means
29a Hook portion
29b Hook portion
31a Loop portion
31b Loop portion
32 End
33 End
34a Strap attachment means
34b Strap attachment means
35a Male snap fastener
35b Female snap fastener
36a Insert outer surface
36b Insert outer surface
38 Insert inner surface
39 Thermal material
41
90 User
91 Bra
92a Bra strap
92b Bra strap
93a Bra cup
93b Bra cup
94a Cup outer surface
94b Cup outer surface
95a Cup inner surface
95b Cup inner surface
96a Breast
96b Breast
100 Thermal Device
102 Pouch
104 Insert
106 Absorbent member
107 Outer surface
108 Hook and loop fasteners
109 Front surface
110 Front member
112 Polyurethane laminate
114 Fabric
116 Inner surface
118 Rear member
120 Polyurethane laminate
122 Fabric
124 Inner surface
200 Device
201 Pouch
202 Absorbent front member
203 Stitching
204 Absorbent rear member
206 Insert
208 Outer surface
210 Hook and loop fasteners
212 Front member inner surface
214 Member
216 Fabric
218 Polyurethane laminate
220 Inner surface
222 Outer surface
224 Rear member inner surface
300 Thermal device
302 Front member
304 Rear member
306 Thermal material
308 Outer surface
310 Fabric
312 Waterproof laminate
314 Inner surface
316 Outer surface
318 Inner surface
320 Stitching
P1 First perimeter
P2 Second perimeter
P3 Third perimeter
P4 Fourth perimeter

What is claimed is:
1. A thermal device capable of providing moist therapy to an affected area, comprising:
    a pouch comprising:
        a first member having a first perimeter and a first waterproof outer surface; and, a second member having a second perimeter and a second waterproof surface where the first and second members are partially joined about the first and second perimeters, respectively, and a cavity is formed between the first and second members;
a removable insert arranged to be disposed within the cavity, the insert comprising:
an insert outer surface;
an insert inner surface; and,
a thermal material encapsulated within the insert inner surface and capable of being heated or cooled; and,
an unperforated moistening absorbent member releasably securable to the first outer surface of the first member via at least one attachment means, said unperforated moistening absorbent member containing no apertures, the unperforated moistening absorbent member configured to be moistened and secured to the pouch configured to contain the insert prior to providing moist therapy.

2. The thermal device of claim 1, wherein the first and second members are at least partially connected via heat-sealing.

3. The thermal device of claim 1, wherein the first and second members are at least partially connected via stitching.

4. The thermal device of claim 1, wherein the at least one attachment means includes at least one hook and loop fastener.

5. The thermal device of claim 1, wherein the thermal material is selected from the group consisting of silica gel, ceramic beads, glass beads, vinyl-based synthetic beads, sodium acetate, sodium polyacrylate, hydroxyethyl cellulose, paraffin, rice, flax seed, barley, and buckwheat.

6. The thermal device of claim 1, wherein:
the first member includes an absorbent first inner surface; and,
the second member includes an absorbent second inner surface.

7. The thermal device of claim 1, wherein:
the second perimeter has a first length;
the moistening absorbent member has a third perimeter which has a second length, wherein the second length is substantially the same as the first length.

8. The thermal device of claim 1, wherein:
the first perimeter has a first length;
the second perimeter has a second length;
the insert has a third perimeter which has a third length, wherein the third length is less than the first and second lengths.

9. The thermal device of claim 1, wherein the at least one attachment means includes a hook fastener.

10. The thermal device of claim 1, wherein the at least one attachment means includes a hook interactive means.

11. A thermal device arranged to be disposed between an article of clothing and an area of skin and capable of providing moist therapy to the area of skin, the thermal device comprising:
a pouch comprising:
an unperforated first member having a first perimeter and a first outer surface arranged to face the article of clothing, wherein the first outer surface is hydrophobic, said unperforated first member containing no apertures; and,
an unperforated second member having a second perimeter and a second moistening absorbent outer surface arranged to contact the area of skin and the first and second members are partially joined about the first and second perimeters, respectively, and a cavity is formed between the first and second members, said unperforated second member containing no apertures; and,
a removable insert arranged to be disposed within the cavity and enclosing thermal material capable of being heated or cooled;
wherein the moistening absorbent outer surface is configured to be moistened prior to providing moist therapy.

12. The thermal device of claim 11, wherein the first and second members are partially joined via heat-sealing.

13. The thermal device of claim 11, wherein the first member includes a first inner surface which is hydrophobic.

14. The thermal device of claim 11, wherein the thermal material is selected from the group consisting of silica gel, ceramic beads, glass beads, vinyl-based synthetic beads, sodium acetate, sodium polyacrylate, hydroxyethyl cellulose, paraffin, rice, flax seed, barley, and buckwheat.

15. The thermal device of claim 13, wherein the second member includes a second inner surface, facing the first inner surface, and the second inner surface is hydrophobic.

16. The thermal device of claim 11, wherein the first perimeter has a first length which is substantially the same as a second length of the second perimeter.

17. The thermal device of claim 11, wherein the first and second perimeters have a first and a second length, respectively, and the insert has a third perimeter which has a third length which is less than the first and second lengths.

18. The thermal device of claim 11, further comprising a waterproofing member securable to the pouch to further prevent moisture from the moist therapy from contacting the article of clothing.

19. A thermal device capable of providing moist therapy to an area of skin, comprising:
an unperforated first member having a first perimeter and a first outer surface comprising a first hydrophobic material, containing no apertures;
an unperforated second member having a second perimeter and a second outer surface comprising a second moistening absorbent material, different than the first hydrophobic material, containing no apertures, wherein the first and second members are directly connected about the first and second perimeters, respectively, and form a chamber therebetween; and,
a non-removable thermal material capable of being heated or cooled disposed within the chamber;
wherein, the moistening absorbent material of the second outer surface is configured to be moistened prior to providing moist therapy.

20. The thermal device of claim 19, wherein the first member includes a first inner surface which is made of a hydrophobic material.

21. The thermal device of claim 19, wherein the thermal material is embodied as a removable insert.

22. The thermal device of claim 19, wherein the thermal material is enclosed by the first and second members.

23. A thermal device capable of providing moist therapy to an area of skin, consisting of:
an unperforated first member having a first perimeter and a first outer surface comprising a first hydrophobic material;
an unperforated second member having a second perimeter and a second outer surface comprising a second moistening absorbent material, different than the first material, wherein the first and second members are joined about the first and second perimeters, respectively, and form a chamber therebetween; and,
a non-removable thermal material capable of being heated or cooled disposed within the chamber;
wherein, the moistening absorbent material of the second outer surface is configured to be moistened prior to providing moist therapy.

\* \* \* \* \*